(12) United States Patent
Gerber et al.

(10) Patent No.: US 9,192,707 B2
(45) Date of Patent: Nov. 24, 2015

(54) ELECTROLYTE AND PH MONITORING FOR FLUID REMOVAL PROCESSES

(75) Inventors: Martin Gerber, Maple Grove, MN (US); John Burnes, Coon Rapids, MN (US); Suping Lyu, Maple Grove, MN (US); Manda R. VenKatesh, Stillwater, MN (US); Bryant Pudil, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 727 days.

(21) Appl. No.: 13/424,479

(22) Filed: Mar. 20, 2012

(65) Prior Publication Data

US 2012/0273420 A1 Nov. 1, 2012

Related U.S. Application Data

(60) Provisional application No. 61/480,539, filed on Apr. 29, 2011, provisional application No. 61/480,544, filed on Apr. 29, 2011, provisional application No. 61/480,541, filed on Apr. 29, 2011, provisional (Continued)

(51) Int. Cl.
*B01D 61/32* (2006.01)
*B01D 61/26* (2006.01)

(Continued)

(52) U.S. Cl.
CPC ............ *A61M 1/1603* (2014.02); *A61B 5/0031* (2013.01); *A61B 5/026* (2013.01);

(Continued)

(58) Field of Classification Search
CPC ..... A61M 1/1696; A61M 1/16; A61M 1/342; A61M 1/34; A61M 2205/70; A61M 1/14; A61M 1/3437; A61M 1/3465; A61M 1/3609; A61M 2205/18; A61M 1/00; A61M 1/1601; A61M 1/1613; A61M 1/3607; A61M 2205/33; A61M 2205/3334; A61M 2230/00; A61M 2230/208; A61M 1/1605; A61M 1/1607; A61M 1/1603; A61M 2230/65; A61M 2230/207; A61M 2205/50; A61M 2205/3303; A61M 2205/04; A61M 2202/0498; B01D 2313/12; B01D 2321/40; B01D 61/00; B01D 61/32; B01D 65/02; A61B 2560/0223; A61B 5/0031; A61B 5/026; A61B 5/0295; A61B 5/053; A61B 5/0537; A61B 5/145; A61B 5/14503; A61B 5/14539; A61B 5/14546; A61B 5/4836; A61B 5/4848; A61B 5/6866; A61B 5/14535; A61B 5/4875; A61B 5/7282
USPC ............... 210/85, 86, 97, 102, 103, 104, 134, 210/141, 143, 252, 257.1, 257.2, 258, 210/321.6, 321.65, 321.71
See application file for complete search history.

(56) References Cited

U.S. PATENT DOCUMENTS 3,608,729 A 9/1971 Haselden
3,669,878 A 6/1972 Marantz (Continued)

FOREIGN PATENT DOCUMENTS

EP 266795 A2 11/1987
EP 0906768 2/2004

(Continued)

OTHER PUBLICATIONS

International Search Report, PCT/US2012/034330 mailed Aug. 28, 2012.

(Continued)

*Primary Examiner* — John Kim
(74) *Attorney, Agent, or Firm* — Hahn & Voight PLLC; Roger C. Hahn; Kenneth J. Collier

(57) ABSTRACT

Methods include monitoring indicators of blood pH or blood electrolyte levels during a blood fluid removal session and adjusting concentrations of pH buffers or electrolytes in dialysate or replacement fluid used during the session based on the monitored indicators. Blood fluid removal systems may employ sensors that monitor blood pH or electrolyte levels to adjust the fluid parameters during a blood fluid removal session.

8 Claims, 8 Drawing Sheets

Related U.S. Application Data application No. 61/480,535, filed on Apr. 29, 2011, provisional application No. 61/480,532, filed on Apr. 29, 2011, provisional application No. 61/480,530, filed on Apr. 29, 2011, provisional application No. 61/480,528, filed on Apr. 29, 2011.

(51) Int. Cl.

| | | |
|---|---|---|
| *A61M 1/16* | (2006.01) | |
| *A61B 5/00* | (2006.01) | |
| *A61B 5/026* | (2006.01) | |
| *A61B 5/053* | (2006.01) | |
| *A61B 5/145* | (2006.01) | |
| *A61M 1/34* | (2006.01) | |
| *B01D 65/02* | (2006.01) | |
| *A61M 1/00* | (2006.01) | |
| *A61B 5/0295* | (2006.01) | |
| *A61M 1/14* | (2006.01) | |
| *B01D 61/00* | (2006.01) | |
| *A61M 1/36* | (2006.01) | |

(52) U.S. Cl.
CPC ............. *A61B 5/0295* (2013.01); *A61B 5/053* (2013.01); *A61B 5/0537* (2013.01); *A61B 5/145* (2013.01); *A61B 5/14503* (2013.01); *A61B 5/14535* (2013.01); *A61B 5/14539* (2013.01); *A61B 5/14546* (2013.01); *A61B 5/4836* (2013.01); *A61B 5/4848* (2013.01); *A61B 5/4875* (2013.01); *A61B 5/6866* (2013.01); *A61B 5/7282* (2013.01); *A61M 1/00* (2013.01); *A61M 1/14* (2013.01); *A61M 1/16* (2013.01); *A61M 1/1601* (2014.02); *A61M 1/1605* (2014.02); *A61M 1/1607* (2014.02); *A61M 1/1613* (2014.02); *A61M 1/34* (2013.01); *A61M 1/342* (2013.01); *A61M 1/3607* (2014.02); *A61M 1/3609* (2014.02); *B01D 61/00* (2013.01); *B01D 61/32* (2013.01); *B01D 65/02* (2013.01); *A61B 2560/0223* (2013.01); *A61M 2202/0498* (2013.01); *A61M 2205/04* (2013.01); *A61M 2205/18* (2013.01); *A61M 2205/33* (2013.01); *A61M 2205/3303* (2013.01); *A61M 2205/3334* (2013.01); *A61M 2205/3523* (2013.01); *A61M 2205/50* (2013.01); *A61M 2205/52* (2013.01); *A61M 2205/60* (2013.01); *A61M 2205/70* (2013.01); *A61M 2230/00* (2013.01); *A61M 2230/207* (2013.01); *A61M 2230/208* (2013.01); *A61M 2230/65* (2013.01); *B01D 2321/12* (2013.01); *B01D 2321/40* (2013.01)

(56) References Cited

U.S. PATENT DOCUMENTS

| | | |
|---|---|---|
| 3,669,880 A | 6/1972 | Marantz |
| 3,850,835 A | 11/1974 | Marantz |
| 3,884,808 A | 5/1975 | Scott |
| 3,989,622 A | 11/1976 | Marantz |
| 4,060,485 A | 11/1977 | Eaton |
| 4,371,385 A | 2/1983 | Johnson |
| 4,374,382 A | 2/1983 | Markowitz |
| 4,381,999 A | 5/1983 | Boucher |
| 4,460,555 A | 7/1984 | Thompson |
| 4,556,063 A | 12/1985 | Thompson et al. |
| 4,581,141 A | 4/1986 | Ash |
| 4,650,587 A | 3/1987 | Polak |
| 4,750,494 A | 6/1988 | King et al. |
| 4,826,663 A | 5/1989 | Alberti |
| 4,828,693 A | 5/1989 | Lindsay |
| 5,127,404 A | 7/1992 | Wyborny et al. |
| 5,284,470 A | 2/1994 | Beltz |
| 5,302,288 A | 4/1994 | Meidl |
| 5,305,745 A | 4/1994 | Zacouto et al. |
| 5,318,750 A | 6/1994 | Lascombes |
| 5,468,388 A | 11/1995 | Goddard |
| 5,683,432 A | 11/1997 | Goedeke et al. |
| 5,744,031 A | 4/1998 | Bene |
| 5,762,782 A | 6/1998 | Kenley |
| 5,944,684 A | 8/1999 | Roberts |
| 6,048,732 A | 4/2000 | Anslyn |
| 6,052,622 A | 4/2000 | Holstrom |
| 6,230,059 B1 | 5/2001 | Duffin |
| 6,254,567 B1 | 7/2001 | Treu |
| 6,321,101 B1 | 11/2001 | Holstrom |
| 6,363,279 B1 | 3/2002 | Ben-Haim et al. |
| 6,602,399 B1 | 8/2003 | Fromherz et al. |
| 6,627,164 B1 | 9/2003 | Wong |
| 6,711,439 B1 | 3/2004 | Bradley et al. |
| 6,818,196 B2 | 11/2004 | Wong |
| 6,878,283 B2 | 4/2005 | Thompson |
| 6,960,179 B2 | 11/2005 | Gura |
| 7,077,819 B1 | 7/2006 | Goldau et al. |
| 7,208,092 B2 | 4/2007 | Micheli |
| 7,276,042 B2 | 10/2007 | Polaschegg |
| 7,566,432 B2 | 7/2009 | Wong |
| 7,575,564 B2 | 8/2009 | Childers |
| 7,704,361 B2 | 4/2010 | Garde |
| 7,736,507 B2 | 6/2010 | Wong |
| 7,776,210 B2 | 8/2010 | Rosenbaum et al. |
| 7,794,141 B2 | 9/2010 | Perry et al. |
| 7,850,635 B2 | 12/2010 | Polaschegg |
| 7,867,214 B2 | 1/2011 | Childers |
| 7,922,686 B2 | 4/2011 | Childers |
| 7,922,911 B2 | 4/2011 | Micheli |
| 7,947,179 B2 | 5/2011 | Rosenbaum et al. |
| 7,967,022 B2 | 6/2011 | Grant |
| 7,981,082 B2 | 7/2011 | Wang |
| 8,034,161 B2 | 10/2011 | Gura |
| 8,070,709 B2 | 12/2011 | Childers |
| 8,096,969 B2 | 1/2012 | Roberts |
| 8,183,046 B2 | 5/2012 | Lu |
| 8,187,250 B2 | 5/2012 | Roberts |
| 8,246,826 B2 | 8/2012 | Wilt |
| 8,273,049 B2 | 9/2012 | Demers |
| 8,292,594 B2 | 10/2012 | Tracey |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,409,441 B2 | 4/2013 | Wilt |
| 8,499,780 B2 | 8/2013 | Wilt |
| 8,518,258 B2 | 8/2013 | Balschat |
| 8,518,260 B2 | 8/2013 | Raimann |
| 8,535,525 B2 | 9/2013 | Heyes |
| 8,580,112 B2 | 11/2013 | Updyke |
| 8,597,227 B2 | 12/2013 | Childers |
| 8,696,626 B2 | 4/2014 | Kirsch |
| 2002/0112609 A1 | 8/2002 | Wong |
| 2003/0080059 A1 | 5/2003 | Peterson |
| 2003/0097086 A1 | 5/2003 | Gura |
| 2003/0105435 A1 | 6/2003 | Taylor |
| 2003/0114787 A1 | 6/2003 | Gura |
| 2004/0019312 A1 | 1/2004 | Childers |
| 2004/0099593 A1 | 5/2004 | DePaolis et al. |
| 2004/0147900 A1 | 7/2004 | Polaschegg |
| 2005/0113796 A1 | 5/2005 | Taylor |
| 2005/0126998 A1 | 6/2005 | Childers |
| 2005/0131332 A1 | 6/2005 | Kelly |
| 2005/0150832 A1 | 7/2005 | Tsukamoto |
| 2005/0236330 A1 | 10/2005 | Nier et al. |
| 2005/0274658 A1 | 12/2005 | Rosenbaum et al. |
| 2006/0195064 A1 | 8/2006 | Plahey |
| 2006/0217771 A1 | 9/2006 | Soykan et al. |
| 2006/0241709 A1 | 10/2006 | Soykan |
| 2007/0007208 A1 | 1/2007 | Brugger |
| 2007/0066928 A1 | 3/2007 | Lannoy |
| 2007/0138011 A1 | 6/2007 | Hofmann |
| 2007/0175827 A1 | 8/2007 | Wariar |

(56) References Cited

U.S. PATENT DOCUMENTS

| | | |
|---|---|---|
| 2007/0179431 A1 | 8/2007 | Roberts et al. |
| 2008/0006570 A1 | 1/2008 | Gura |
| 2008/0021337 A1 | 1/2008 | Li et al. |
| 2008/0053905 A9 | 3/2008 | Brugger |
| 2009/0020471 A1 | 1/2009 | Tsukamoto |
| 2009/0127193 A1 | 5/2009 | Updyke |
| 2009/0281484 A1 | 11/2009 | Childers |
| 2009/0282980 A1 | 11/2009 | Gura |
| 2010/0004588 A1 | 1/2010 | Yeh |
| 2010/0010429 A1 | 1/2010 | Childers |
| 2010/0078381 A1 | 4/2010 | Merchant |
| 2010/0078387 A1 | 4/2010 | Wong |
| 2010/0084330 A1 | 4/2010 | Wong |
| 2010/0114012 A1 | 5/2010 | Sandford |
| 2010/0130906 A1 | 5/2010 | Balschat |
| 2010/0168546 A1 | 7/2010 | Kamath |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0312174 A1 | 12/2010 | Hoffman |
| 2011/0009798 A1 | 1/2011 | Kelly et al. |
| 2011/0017665 A1 | 1/2011 | Updyke |
| 2011/0077574 A1 | 3/2011 | Sigg et al. |
| 2011/0079558 A1 | 4/2011 | Raimann |
| 2011/0087187 A1 | 4/2011 | Beck |
| 2011/0130666 A1 | 6/2011 | Dong et al. |
| 2011/0184340 A1 | 7/2011 | Tan |
| 2011/0208105 A1* | 8/2011 | Brandl et al. ............... 604/5.01 |
| 2011/0272337 A1 | 11/2011 | Palmer |
| 2012/0083729 A1 | 4/2012 | Childers |
| 2012/0085707 A1 | 4/2012 | Beiriger |
| 2012/0115248 A1 | 5/2012 | Ansyln |
| 2012/0220528 A1 | 8/2012 | VanAntwerp |
| 2012/0258546 A1 | 10/2012 | Marran |
| 2012/0273415 A1 | 11/2012 | Gerber |
| 2012/0277546 A1 | 11/2012 | Soykan et al. |
| 2012/0277551 A1 | 11/2012 | Gerber |
| 2012/0277604 A1 | 11/2012 | Gerber |
| 2012/0277655 A1 | 11/2012 | Gerber |
| 2013/0037465 A1 | 2/2013 | Heyes |
| 2013/0199998 A1 | 8/2013 | Kelly |
| 2013/0213890 A1 | 8/2013 | Kelly |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0018728 A1 | 1/2014 | Plahey |
| 2014/0042092 A1 | 2/2014 | Akonur |
| 2014/0088442 A1 | 3/2014 | Soykan et al. |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0220699 A1 | 8/2014 | Pudil |

FOREIGN PATENT DOCUMENTS

| | | |
|---|---|---|
| EP | 1450879 | 10/2008 |
| EP | 1592494 B1 | 6/2009 |
| EP | 2388030 | 11/2011 |
| EP | 1345856 B1 | 3/2013 |
| EP | 2344220 B1 | 4/2013 |
| WO | 9937342 | 7/1999 |
| WO | 0057935 | 10/2000 |
| WO | 03043677 A2 | 5/2003 |
| WO | 03043680 | 5/2003 |
| WO | 03051422 A2 | 6/2003 |
| WO | 2004008826 | 1/2004 |
| WO | 2004009156 | 1/2004 |
| WO | 2004064616 A2 | 8/2004 |
| WO | 2005123230 A2 | 12/2005 |
| WO | 200701064 A2 | 1/2007 |
| WO | 2007089855 A2 | 8/2007 |
| WO | 2009026603 | 3/2009 |
| WO | 2009026603 A1 | 3/2009 |
| WO | 2009157877 | 12/2009 |
| WO | 2009157878 | 12/2009 |
| WO | 2012148781 | 11/2012 |
| WO | 2012148786 | 11/2012 |
| WO | 2012148789 | 11/2012 |
| WO | 2012162515 A2 | 11/2012 |
| WO | 2012172398 | 12/2012 |
| WO | 2013019179 A1 | 2/2013 |
| WO | 2013019994 | 2/2013 |
| WO | 2013025844 | 2/2013 |
| WO | 2013028809 A3 | 2/2013 |
| WO | 2013103607 A1 | 7/2013 |
| WO | 2013103906 | 7/2013 |
| WO | 2013114063 A | 8/2013 |
| WO | 2013121162 A1 | 8/2013 |
| WO | 2014066254 | 5/2014 |
| WO | 2014066255 | 5/2014 |
| WO | 2014077082 | 5/2014 |
| WO | 2014121162 | 8/2014 |
| WO | 2014121163 | 8/2014 |
| WO | 2014121167 | 8/2014 |
| WO | 2014121169 | 8/2014 |

OTHER PUBLICATIONS

International Search Report, PCT/US2012/034333 mailed Aug. 29, 2012.

Roberts, The regenerative dialysis (REDY) sorbent system, Nephrology, 1998, 275-278 : 4.

Bleyer, et. al., Sudden and cardiac death rates in hemodialysis patients, Kidney International, 1999, 1553-1559 : 55.

Weiner, et. al., Article: Cardiac Function and Cardiovascular Disease in Chronic Kidney Disease, Book: Primer on Kidney Diseases (Author: Greenberg, et al), 2009, 499-505, 5th Ed., Saunders Elsevier, Philadelphia, PA.

Ronco, et. al., Cardiorenal Syndrome, J. Am. Coll. Cardiol., 2008, 1527-1539 : 52.

Wang, Fundamentals of intrathoracic impedance monitoring in heart failure, Am. J. Cardiology, 2007, 3G-10G : Suppl.

Siegenthalar, et. al., Pulmonary fluid status monitoring with intrathoracic impedance, Journal of Clinical Monitoring and Computing, 2010, 449-451 : 24.

MacLean, et. al., Effect of hindlimb contraction on pressor and muscle interstitial meabolite responses in the cat, J. App. Physiol., 1998, 1583-1592, 85(4).

Overgaard, et. al., Activity-induced recovery of excitability in K+-depressed rat soleus muscle, Am. J. Physiol. Regulatory Integrative Comp. Physiol., 2001, R48-R55, vol. 280.

Overgaard, et. al., Relations between excitability and contractility in rate soleus muscle: role of the NA+-K+ pump and NA+-K+ gradients, Journal of Physiology, 1999, 215-225, 518(1).

Leifer, I., et al., A Study on the Temperature Variation of Rise Velocity for Large Clean Bubbles, J. Atmospheric & Oceanic Tech., vol. 17, pp. 1392-1402, (2000).

Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.

Talaia, MAR, Terminal Velocity of a Bubble Rise in a Liquid Column, Talaia, World Acad. of Sci., Engineering & Tech., vol. 28, pp. 264-268, (2007).

The FHN Trial Group. In-Center. Hemodialysis Six Times per Week versus Three Times per Week, New England Journal of Medicine, 2010.

PCT/US2014/014357 International Search Report and Written Opinion, (May 2014).

Coast, et al. 1990, An approach to Cardiac Arrhythmia analysis Using Hidden Markov Models, IEEE Transactions on Biomedical Engineering. 1990, 37 (9):826-835.

(56) References Cited

OTHER PUBLICATIONS

PCT/US2012/034330, International Preliminary Report on Patentability, Oct. 29, 2013.

PCT/US2012/034333, International Preliminary Report on Patentability, Oct. 29, 2013.
PCT/US2012/034333, International Search Report, Aug. 29, 2013.

* cited by examiner

ELECTROLYTE AND PH MONITORING FOR FLUID REMOVAL PROCESSES

RELATED APPLICATION

This application claims priority to U.S. Provisional Application No. 61/480,539, U.S. Provisional Application No. 61/480,544, U.S. Provisional Application No. 61/480,541, U.S. Provisional Application No. 61/480,535, U.S. Provisional Application No. 61/480,532, U.S. Provisional Application No. 61/480,530, and U.S. Provisional Application No. 61/480,528, wherein each priority application was filed Apr. 29, 2011, wherein each priority application is hereby incorporated by reference in its entirety to the extent that it does not conflict with the disclosure presented herein.

FIELD

The present disclosure relates generally to devices, systems and methods for monitoring indicators of electrolytes or pH in patients for which blood cleaning or fluid removal is indicated, such as patients suffering from kidney disease or heart failure.

BACKGROUND

Patients who undergo hemodialysis or other procedures that remove solutes and fluid from the blood often die of cardiac complications. Many factors may contribute to such death, including stress placed on the heart due to the increased blood fluid volume in these patients. Increased fluid concentrations and inability to remove waste products from the blood, in some cases, can also contribute to electrolyte and pH imbalance that can affect cardiac contractility and efficiency. Further, rapid changes in fluid volume or pH or electrolyte concentration of the blood during hemodialysis or other fluid removal processes may place additional stress on the heart and may contribute to the high rate of morbidity for patients who undergo blood fluid removal procedures.

When a patient reaches a point where routine blood fluid removal procedures are prescribed, the patient undergoes periodic examinations that allow a healthcare provider to set various parameters of the blood fluid removal procedures, such as the profile of fluid removal, the composition of dialysate or replacement fluid employed, and the like. These examinations typically occur once a month in accordance with current standards of care.

Hemodialysis or similar procedures may occur three to four times a week. Thus, the patient may undergo 10 to 15 or more blood fluid removal sessions before the prescription or parameters are changed. It is possible, for example, that a prescription with regard to a dialysate electrolyte and pH buffer composition will not be appropriate for a patient several days or weeks after the prescription is set. Accordingly, it may be desirable to more frequently determine whether the electrolyte or pH concentration of a fluid used in blood fluid removal sessions is appropriate. In addition, it may be desirable to adjust the concentration or composition of the fluid during a blood fluid removal session in a manner that may improve patient health and reduce morbidity.

SUMMARY

This disclosure, among other things, describes devices, systems and methods for monitoring indicators of pH or electrolytes in patients for which blood fluid removal sessions are indicated. The monitoring may occur during a blood fluid removal session, and the concentration or composition of buffer or electrolytes may be adjusted based on monitored data acquired during the blood fluid removal session. By monitoring pH or electrolytes, the dialysate of replacement fluid may be adjusted during a session to enhance patient safety.

In various embodiments described herein, a method includes initiating a blood fluid removal procedure for a patient in need thereof. The procedure includes use of a fluid selected from a dialysate fluid or a replacement fluid. The fluid has an initial pH buffer composition or electrolyte composition. The method further includes monitoring an indicator of blood electrolyte concentration or blood pH of the patient during the blood fluid removal session, and adjusting the pH buffer composition or the electrolyte composition of the fluid based on a value of the monitored indicator. The monitoring may be of blood before or after the blood has passed through the blood fluid removal device, or may be of fluid removed from the blood. In some embodiments, data acquired from monitoring performed on blood before and after passing through the blood fluid removal device is compared to data acquired from fluid (e.g., dialysate) before and after passing through blood fluid removal media of the device, and based on the comparison, the pH buffer composition or the electrolyte composition of the fluid is adjusted.

In embodiments, a system includes a blood fluid removal device, which has (i) an inlet for receiving blood from a patient, (ii) an outlet for returning blood from the patient, (iii) a medium for removing fluid and contaminants from the blood, the medium being positioned between the inlet and the first outlet, and (iv) a fluid source for carrying a fluid, where the fluid is selected from dialysate and replacement fluid. If the fluid is dialysate, the fluid source carries the fluid to the medium. If the fluid is replacement fluid, the fluid source carries the fluid to the blood after the blood exits the medium. The system further includes (i) a concentrate source for housing a concentrate solution comprising concentrated electrolyte or pH buffer, (ii) a concentrate flow control element for controlling the rate that the concentrate solution enters the fluid source; (iii) a sensor for monitoring an indicator of blood pH or blood electrolyte concentration; and (iv) control electronics in operable communication with the sensor and the concentrate flow control element. The control electronics are configured, via the concentrate flow control element, to adjust the rate at which the concentrate solution enters the fluid source based on data obtained from the sensor.

In embodiments, a system includes (i) a medium housing defining a major chamber; (ii) a blood flow removal membrane disposed in the housing and sealingly dividing the major chamber into first and second minor chambers; (iii) a first inlet and a first outlet in fluid communication with the first minor chamber, wherein the system is configured such that blood enters the first minor chamber through the first inlet and exits the first minor chamber through the first outlet; (iv) a second inlet and a second outlet in fluid communication with the second minor chamber, wherein the system is configured such that dialysate enters the second minor chamber through the second inlet and exits the second minor chamber through the second outlet; (vi) a dialysate regeneration medium in fluid communication with and disposed in a dialysate flow path between the second inlet and the second outlet; (vii) a concentrate source for housing a concentrate solution comprising concentrated electrolyte or pH buffer; (viii) a concentrate flow control element for controlling the rate that the concentrate solution enters the dialysate flow path downstream of the dialysate regeneration medium and upstream of the second inlet; (ix) a sensor configured to monitor an indicator of electrolyte concentration or pH of dialysate in the dialysate flow path downstream of the dialysate regeneration medium and upstream of the second inlet; and (x) control electronics in operable communication with the sensor and the concentrate flow control element, wherein the control electronics are configured, via the concentrate flow control element, to adjust the rate at which the concentrate solution enters the dialysate flow path based on data obtained from the sensor.

One or more embodiments of the systems, devices and methods described herein may provide one or more advantages over prior systems, devices and methods for blood fluid removal in patients. Such advantages will be apparent to those skilled in the art upon reading the following detailed description.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

FIG. 7; open loop: FIG. 8) for controlling flow of concentrate into fluid for use in a blood fluid removal process based on monitored pH or electrolytes.

Figure 1:
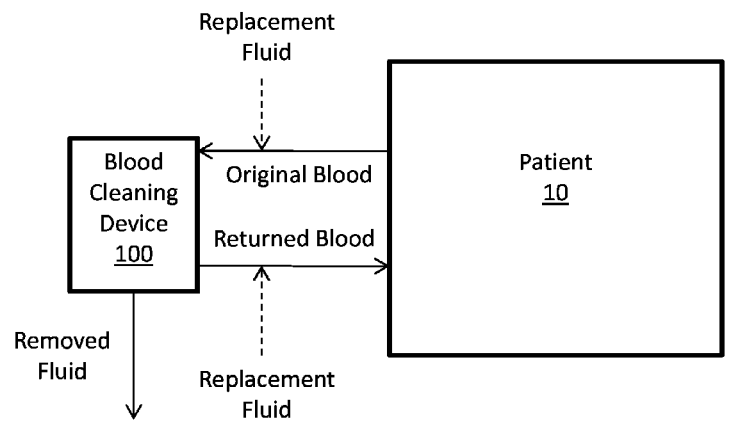
FIGS. 1-3 are schematic block diagrams showing interaction of blood fluid removal devices with a patient showing flow of blood (dashed arrows) and fluid (solid arrows), which blood fluid removal devices may be used in various embodiments described herein.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

As used herein, a "patient for which a blood fluid removal session is indicated" is a patient that has undergone, is undergoing, or is likely to undergo at least one blood fluid removal session. In general, such patients are fluid overloaded patients, such as patients suffering from heart failure, chronic kidney disease, or acute kidney failure. Often such patients are stage 3 to stage 5 chronic kidney disease patients, are unresponsive or under-responsive to diuretics, or the like.

As used herein, a "blood fluid removal process," or the like, refers to a process from which fluid is removed from blood of a patient and the blood is returned to the patient. In most cases, the blood is also cleaned; i.e., waste products are removed from the blood and cleaned blood is returned to the patient. Examples of blood fluid removal processes include ultrafiltration, hemofiltration, hemodialysis, hemodiafiltration, peritoneal dialysis, and the like. Any patient for which blood fluid removal is indicated may benefit from the devices, systems and methods described herein.

This disclosure relates to, among other things, systems and methods for monitoring indicators of pH or electrolyte concentrations in patients for which a blood fluid removal process is indicated. In embodiments, the sensors are configured and positioned to monitor pH or electrolytes in one or more of (i) blood of the patient before the blood enters a fluid removal or cleaning medium of the blood fluid removal device; (ii) blood of the patient before after blood exits the medium before being returned to the patient; (iii) fluid removed from the blood of the patient after passing through the medium; (iv) fluid, such as dialysate, before entering the medium; (v) fluid upstream or downstream of the addition of a concentrate for use in altering the composition of the fluid (e.g., dialysate or replacement fluid); (vi) or the like. Additional discussion with regard to sensor placement and use of such sensors will follow. First, however, a brief discussion of blood fluid removal devices or systems that may be used in accordance with the teachings presented herein is presented.

Any suitable device or system for removing fluid, or fluid and contaminants, from blood may be used in accordance with the teachings presented herein. The devices, or components thereof, may be traditional large counsel-type, wearable, or implantable.

Figure 2:
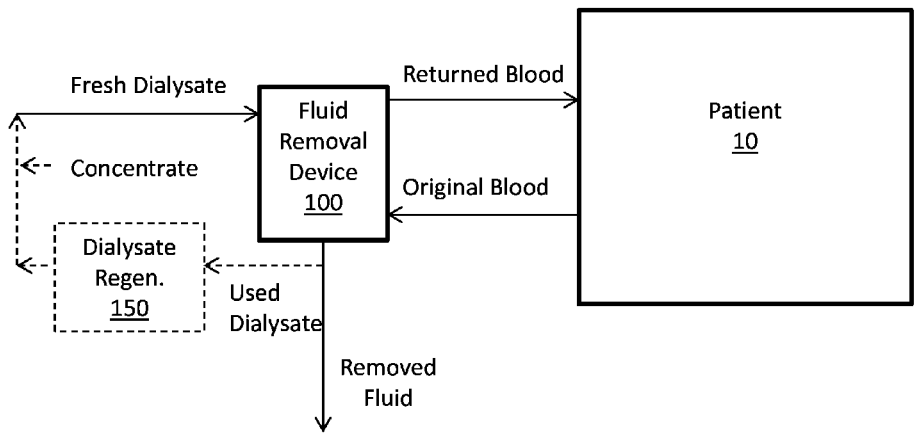
Figure 3:
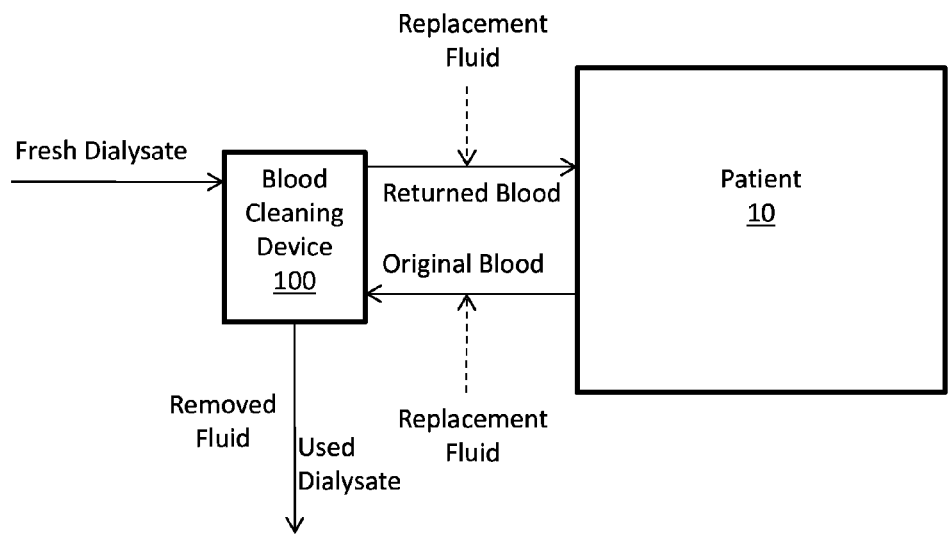

Block diagrams of some example devices and systems are shown in FIGS. 1-3. As shown in FIG. 1, blood may be removed from a patient 10 and fluid may be removed via a blood fluid removal device 100 and returned to the patient 10. Removed fluid may be diverted. In some embodiments where the blood fluid removal device 100 or system, or components thereof, are implanted, the removed fluid may be diverted to the patient's bladder. Examples of blood fluid removal devices 100 that may operate as depicted in FIG. 1 are ultrafiltration and hemofiltration devices. Examples of such devices and components thereof that may be employed in accordance with the teachings presented herein are well known in the art. It will be understood that peritoneal dialysis, where dialysate is introduced into the peritoneal cavity, may also be employed.

With some of such devices, replacement fluid may be introduced into the patient's blood if fluid is removed from the blood by the device 100 at too great of a rate or amount. The replacement fluid may be added to the original blood before fluid removal or may be added to the blood after initial fluid removal and prior to return to the patient's cardiovascular system. Preferably, the replacement fluid is added after initial fluid removal. The pH and electrolyte concentration of the replacement fluid may be set or adjusted, e.g. as described in more detail below, based on monitoring of pH or electrolytes of the patient.

As shown in the embodiment depicted in FIG. 2, the blood fluid removal device 100 may employ dialysate to assist in removal of contaminants from the patient's blood and in maintaining proper pH and electrolyte balance. The pH or electrolyte concentration of the dialysate may be set or adjusted, e.g. as described in more detail below, based on monitoring of pH or electrolytes. Used dialysate and fluid removed from the blood may be diverted. In some embodiments, particularly where the blood fluid removal device 100 or system or components thereof are wearable or implantable, the used dialysate and removed fluid, or a portion thereof, may be regenerated (indicated by dashed lined regeneration system 150) to produce fresh dialysate for re-use in the blood fluid removal process. One system for regeneration of dialysate is the REDY system, such as described in Roberts, M, "The regenerative dialysis (REDY) sorbent system," *Nephrology* 4:275-278, 1998, which system may be employed or readily modified for use in embodiments described herein. As shown in FIG. 2, a concentrate may be added to the regenerated dialysate to adjust the pH and electrolytes of the regenerated dialysate to an amount suitable for re-use as fresh dialysate.

Regardless of whether the dialysate is regenerated, systems and devices that operate in a manner shown in the embodiment of FIG. 2 include hemodialysis and hemodiafiltration systems. Examples of such devices and components thereof that may be employed in accordance with the teachings presented herein are well known in the art. It will be understood that peritoneal dialysis, where the dialysate is introduced into peritoneal cavity may also be employed.

As shown in FIG. 3, in cases where the blood fluid removal device 100 of FIG. 2 removes fluid from the blood at too high of a rate, replacement fluid may be introduced into the patient's blood, upstream or downstream of fluid removal, e.g. as described above with regard to FIG. 1.

Regardless of the device or blood fluid removal process employed, it is important to ensure that the blood pH and electrolyte concentrations are within suitable ranges. If blood electrolyte concentrations are not within suitable ranges, problems with cardiac contractility, efficiency and the like may occur. If the pH is not within a suitable range, acidosis may result, which can result in disruption of cell membranes and denaturation of proteins. In either case, if ranges of blood electrolytes and pH are not properly controlled, the patient's health may be at risk. For example, sudden and cardiac death (including death from congestive heart failure, myocardial infarction, and sudden death) are common in hemodialysis patients. See Bleyer et al, "Sudden and cardiac death rated in hemodialysis patients," *Kidney International*, (1999), 55:1552-1559.

Accordingly, one goal of hemodialysis, ultrafiltration, and the like is to ensure that the patient's blood pH and electrolyte concentrations are within acceptable ranges. Typical ranges of pH and blood electrolyte concentration that are desired during or following a blood fluid removal session are provided in Table 1 below. As indicated in Table 1, concentrations of various acids or bases (or salts or hydrates thereof) are often important in determining the pH of blood. Accordingly, some typical target concentrations of such acids, bases are presented in Table 1.

TABLE 1

Typical target ranges for pH and electrolytes
(ref. Medical Surgical Nursing, 7$^{th}$ Ed., 2007)

|  | Target Range |
| --- | --- |
| pH | 7.35-7.45 |
| Phosphate | 2.8-4.5 mg/dL |
| Bicarbonate | 22-26 mEq/L |
| Cl$^-$ | 96-106 mEq/L |
| Mg$^{2+}$ | 1.5-2.5 mEq/L |
| Na$^+$ | 135-145 mEq/L |
| K$^+$ | 3.5-5.0 mEq/L |
| Ca$^{2+}$ | 4.5-5.5 mEq/L |

However, it will be understood that the target for a particular patient may be different from the values presented in Table 1 for one or more electrolyte or pH. It will also be understood that buffers are typically employed to maintain proper blood pH.

Some suitable buffers that may be used in fluid, such as replacement fluid or dialysate, include bicarbonate, acetate, citrate, lactate, amino acid and protein buffers. The concentration and composition of the buffers and components thereof may be adjusted based on monitored pH of the patient's blood. Similarly, the concentration of electrolytes such as sodium, potassium, calcium, and chloride in replacement fluid or dialysate may be set or altered based the monitored levels of electrolytes.

Any suitable sensor may be employed to monitor pH or electrolytes. For example and referring to FIG. 4, a block diagram showing some components that a sensing device 200 may include is depicted. The sensing device 200 is shown as a stand-alone device in FIG. 4, but is will be understood that the device, one or more components thereof, may be incorporated into other devices, such as a blood fluid cleaning device. The sensor 200 depicted in FIG. 4 has a housing 299 (which can be shared with another device if the sensor, or portion thereof, is incorporated into the other device) for containing various electronic components 296, 297, 289, 295. Sensing circuitry 296, such as analog-to-digital convertor, band-pass filter, or the like, is operably coupled to power supply 297 (which, again may be shared) and control electronics 295 (which may be shared), which include a processor 294 and a memory 293 for storing sensed data and processor instructions. Sensing circuitry 296 is also operably coupled to transducer 205, such as an ion selective electrode, via lead 207. In some embodiments (not shown), the device 200 is leadless, and the transducer 207 or ion selective electrode is exposed through housing 299. Control electronics 295 are operably coupled to power supply 297 and to communication circuitry 289 for communicating with another device external. In cases where the sensor 200 is a stand-alone device, communication circuitry may be used to communicate with a blood fluid removal device or a device in communication with a blood fluid removal device to transmit data acquired from the sensor to the blood fluid removal device.

Any suitable transducer may be employed to detect pH or electrolytes. In embodiments, the transducer is an ion selective electrode configured to detect $H^+$ ions, $K^+$ ions, $Na^+$ ions, $Ca^{2+}$ ions, $Cl^-$ ions, phosphate ions, magnesium ions, acetate ions, amino acids ions, or the like. Such electrodes, and components of sensors employing such electrodes, are known in the art and may be employed, or modified to be employed, for use in the monitoring described herein.

In some embodiments, one or more sensors are employed to detect one or more ions to gauge pH or electrolytes in the blood. In some embodiments, a sensor may have more than one transducer, even if leadless, that may monitor more than one ionic species. By measuring more than one ionic species, a more detailed understanding of the levels of various electrolytes or blood components may be had. For example, in some patients in some situations, one electrolyte may be at elevated levels while another may be at reduced levels. In some embodiments, more than one sensor for the same ion is employed for purposes of result confirmation and redundancy, which can improve reliability and accuracy. In some embodiments, sensors for the same ion may be configured to accurately detect different ranges of concentrations of the ion. In embodiments, more than one transducer is present in a single unit. This allows for convenient data collection and circuitry, as all the data may be collected in one place at the same time. Further, the multiple transducers may share the same fluid collection mechanism (e.g., a microdialyzer in the case of an implant), and if needed or desired, may share the same data processing and memory storage components.

Figure 5:
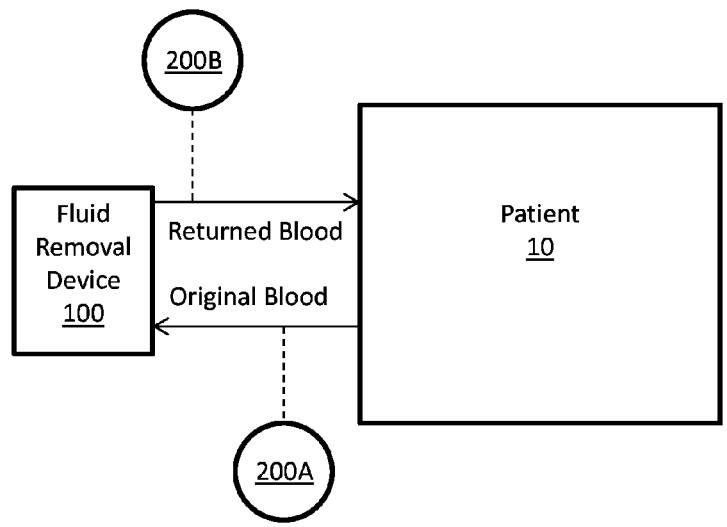
FIGS. 5-6 are schematic block diagrams showing sensors and blood flow between patients and a blood fluid removal devices.

A sensor (or transducer) may be placed at any suitable location for purposes of monitoring electrolytes or pH. For example, and with reference to FIG. 5, an example of a blood fluid removal system and sensors is depicted. One or more of sensors 200A, 200B may be employed. As shown in FIG. 5, a pH or electrolyte sensor 200A may be located external to the patient 10 and configured to monitor pH or electrolyte levels in the blood before the blood enters the blood fluid removal device 100 (or before entering blood fluid removal medium, as will be discussed below in more detail). For example, sensor 200A may be positioned such that a transducer is placed within a catheter carrying blood from the patient 10 to the blood fluid removal device 100 or blood fluid removal media.

Data acquired from a sensor 200A upstream of the fluid delivery device 100 or blood fluid removal media provides an indication of the actual status of the patient 10. As a blood fluid cleaning session progresses, data acquired from a sensor 200A upstream of the fluid delivery device 100 or medium can be used to determine whether blood pH and electrolytes are approaching target ranges or to determine the rate at which pH and electrolytes are changing in the patient as a result of the blood fluid removal process. While not intending to be bound by theory, it is possible that too rapid of a change in pH or electrolyte concentrations can lead to patient hypotension or sudden death that is seen in patient populations that undergo blood fluid removal processes. By monitoring and controlling the rate of change of pH or electrolyte changes in the blood of a patient during the blood fluid removal session, perhaps the incidence of crashing or sudden death can be reduced.

In some embodiments, a sensor 200B is located external to the patient 10 and configured to monitor pH or electrolyte levels in the blood after the blood exits the blood fluid removal device 100 (or after exiting the blood fluid removal medium) and before being returned to the patient 10. For example, sensor 200B may be positioned such that a transducer is placed within a catheter carrying blood from the blood fluid removal device 100 (or medium) to the patient 10. Such a downstream sensor 200B may be used to ensure that pH and electrolyte levels of blood to be returned to the patient are not out of range. If the detected levels are out of range or are tending towards out of range, adjustments to pH and electrolyte concentrations can be made to fluid (dialysate or replacement fluid) to avoid introducing fluid into the patient 10 that may cause or exacerbate a cardiac problem associated with electrolyte or pH levels that are too high or too low.

In some embodiments, the system employs both an upstream sensor 200A and a downstream sensor 200B. With such systems, the pH or electrolyte levels detected upstream and downstream may be compared, and the compared data may be used to adjust the pH or electrolyte concentration or composition of fluid employed during a blood fluid removal session. The compared data may also be used to determine the rate of change of blood electrolyte concentration or pH. By way of example, prior to a blood fluid removal session or in the early parts of such a session, the patient is typically fluid over-loaded and the concentration of electrolytes may be low (due to the increased fluid volume). It may be appropriate to allow a slightly higher than target concentration electrolyte to be introduced back into the patient when the patient's electrolyte levels are low. However, as the patient's electrolyte levels (as measured by upstream sensor 200A) approach target levels, the electrolyte levels in the returned blood (as measured by downstream sensor 200B) should within target range. Monitoring both upstream and downstream will allow for adjustments and checks on progress that may not be attainable by monitoring only one or the other.

Figure 6:
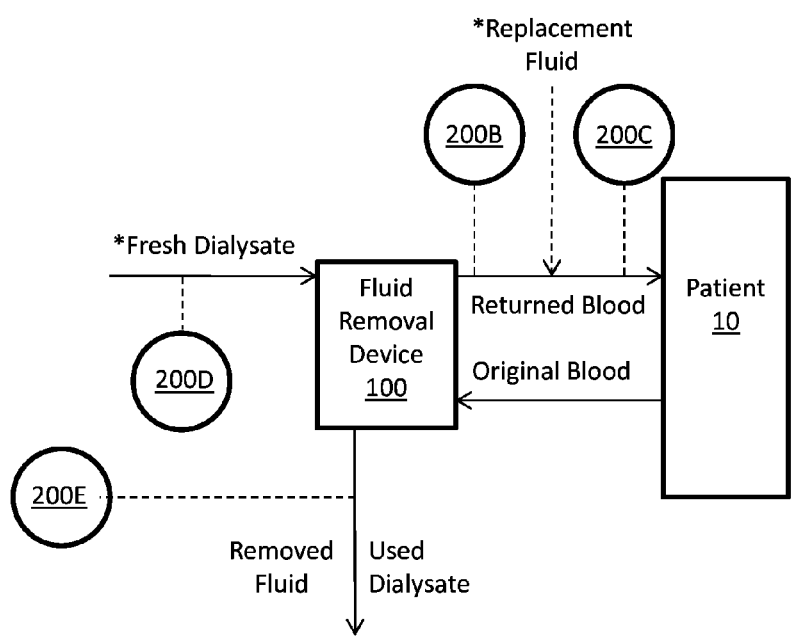

Referring now to FIG. 6, a system employing sensors 200B, 200C, 200D, and 200E in alternative or additional locations is show. Any one or more of such sensors 200B, 200C, 200D, and 200E may be employed. The system may also employ one or more downstream sensors as described with regard to FIG. 5, but are not shown in FIG. 6. A brief discussion of some possible configurations and uses of sensors 200B, 200C, 200D, and 200E is provided herein. However, it will be understood that meaningful data may be obtained from configurations other than those described below.

In embodiments, the system (e.g., the system depicted in FIG. 6) employs two upstream sensors 200B and 200C. The first upstream sensor 200B is positioned to monitor pH or electrolyte levels in the blood after it exits the blood fluid removal device 100 or medium but before replacement fluid is added. The second sensor 200C is positioned to monitor pH or electrolyte levels of the blood after the replacement fluid is added and before the blood is returned to the patient 10. The first sensor 200B may be used to determine what adjustments may be need to pH and electrolyte levels, and the second sensor 200C may be used to verify that the appropriate adjustments were made to achieve the desired pH and electrolyte concentrations prior to returning the blood to the patient.

In embodiments, the system employs a sensor 200E to monitor pH or electrolytes removed from the blood of the patient after exiting the blood fluid removal device 100 or medium, and may include a sensor 200D configured and positioned to monitor pH or electrolytes of fluid (in the depicted case, dialysate) prior to entering the blood fluid device 100 or medium. By monitoring the pH or electrolytes in the fluid as it leaves the device 100 or medium (or the differential pH or electrolyte levels from before entering the device or medium and after exiting the device or medium), the pH or levels of electrolytes (or change in pH or electrolytes) exiting the device 100 or medium may be used to predict the blood pH and electrolyte levels without having to measure the levels in the blood directly. In cases where pH or electrolytes are detected in fluid other than blood and used to derive or predict pH or electrolyte levels or changes in blood, such detection serves as an "indicator" of blood pH or electrolytes. Of course, direct detection in blood also serves as an indicator of blood pH or electrolytes.

Regardless of which sensors 200A-E (see, FIGS. 4-6) are employed, data acquired from the sensors may be used to adjust the pH or electrolyte concentrations of fluid (e.g. dialysate or replacement fluid) used during the dialysis session. In some embodiments, the concentrations of dialysate or replacement fluid are varied and the patient's response to the varying concentrations, as measured by one or more of sensors, is used to determine how best to proceed with further adjustments. In essence, the system may be configured to learn what works best for the particular patient 10. For example, dialysate or replacement fluid having different buffer concentrations or compositions or different electrolyte concentrations may be used during an initial blood fluid session or early in a blood fluid session. The patient's response to these different fluids can be monitored via sensors, and the system can learn what works best for the patient. For example, the system can determine whether the use of the different fluids resulted in the patient's blood levels approaching target levels or deviating from target levels, as well as the rate at which the approach or deviate from target ranges. Based on the initial sessions or stages, the system may begin to predict how to react to a particular monitored pH or electrolyte level for the patient and adjust the fluid pH and electrolyte concentrations accordingly.

Figure 4:
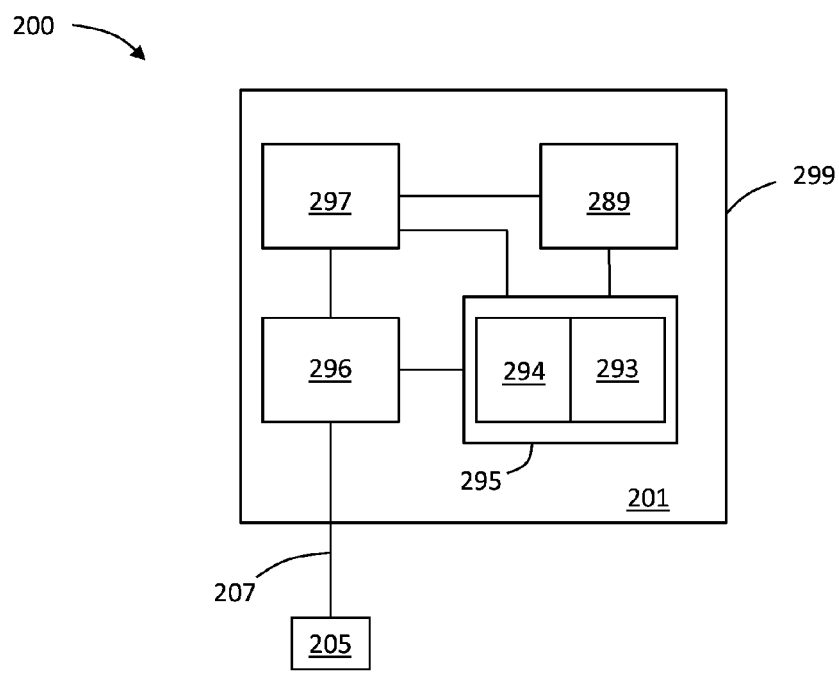
FIG. 4 is a schematic block diagram showing some selected components of an embodiment of a sensor device.

Support for these amendments in the specification can be found in at least FIGS. 4-6 of the originally filed drawings.

Figure 7:
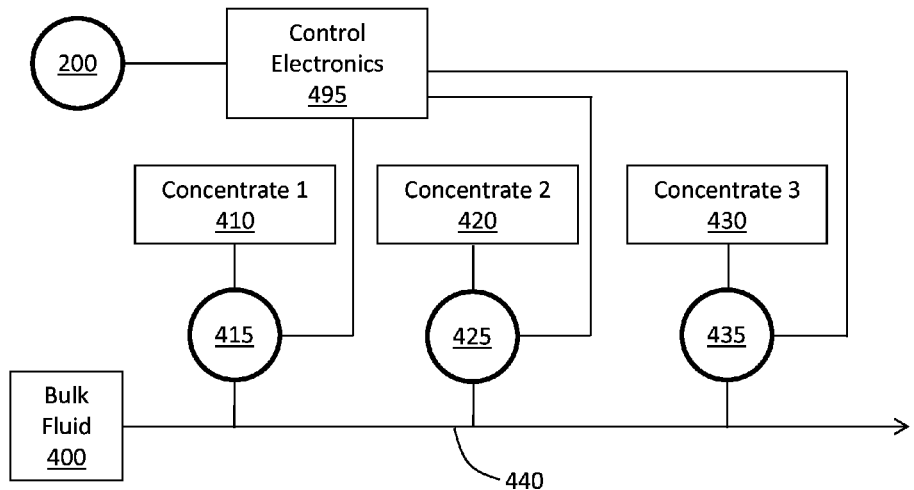
FIGS. 7-8 are schematic block diagrams showing flow paths and some control mechanisms (closed loop.

The pH and electrolyte concentration of the fluid (dialysate or replacement fluid) may be adjusted in any suitable manner. For example and with reference to FIGS. 7-8, some representative components of an example of a closed-loop system (FIG. 7) and an open-loop system (FIG. 8) for adjusting pH and electrolyte concentrations of fluid are shown. With reference to FIG. 7, data from one or more sensor 200 is presented to control electronics 495, which are configured to control flow control elements 415, 425, 435, such as valves. The electronically controllable flow control elements 415, 425, 435 are in fluid communication with supplies of concentrated electrolyte or buffer solutions 410, 420, 430 and with fluid line 440, which may be a catheter for carrying fresh dialysate or a catheter for carrying replacement fluid. The electronically controllable flow control elements 415, 425, 435, via control electronics 495, control the rate at which the concentrates 410, 420, 430 flow into the fluid line 440. The concentrates 410, 420, 430 are added to bulk fluid 400 to adjust the concentration of electrolytes or the pH of the bulk fluid (and thus the blood).

Figure 8:
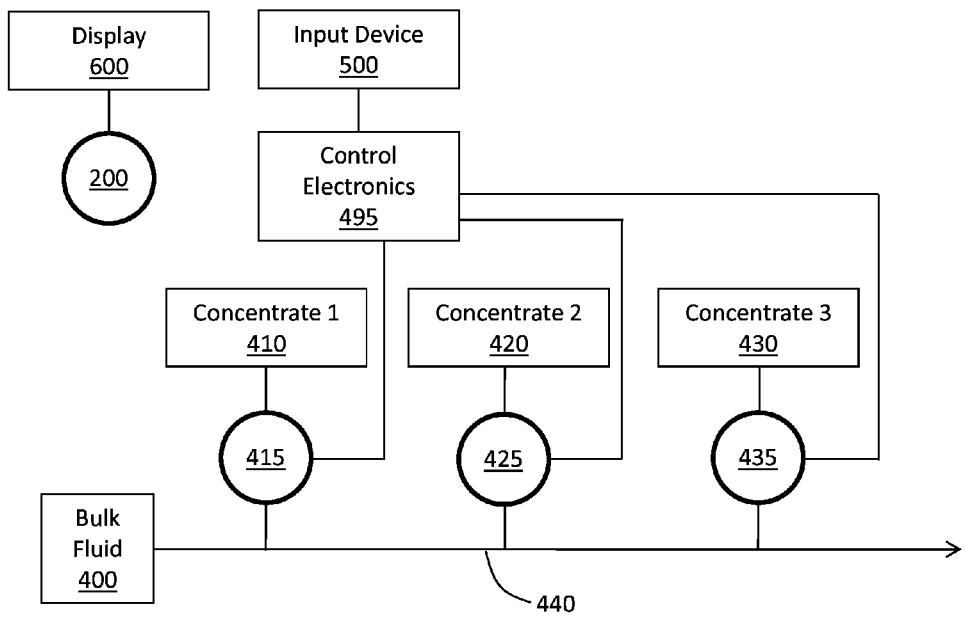

Referring now to FIG. 8, data from one or more sensor 200 may be processed and appropriate information presented on a display 600, which may be a part of the blood fluid removal device, a separate computer, or the like. A healthcare provider may use the information presented on the display 600 to adjust the concentration of electrolytes or pH. This can be done, for example, by transmitting appropriate instructions to the control electronics via an input device 500. Any suitable input device 500 may be used. For example, input device 500 may be a keyboard, a computer, a tablet, a personal data assistant, a physician programmer, or the like. In some embodiments, the input device 500 is the display 600; e.g., where the display 600 is a touch screen device. Regardless of how the instructions are input, the control electronics 495 can control flow control elements 415, 425, 435 to control the amount of concentrate 410, 420, 430 introduced to bulk fluid 400, which may be dialysate or replacement fluid.

Any number of suitable concentrates may be used. For example, one concentrate may be sufficient with higher amounts being added when the electrolytes are determined to be low in the patient's blood, and smaller amounts being added when the electrolytes are determined to be high in the patient's blood. More than one concentrate may be used when it is desired to, for example, control pH and electrolyte concentration independently or to control concentration of different electrolytes independently. In embodiments, the number of concentrates is the same as the number of ion species (pH and electrolytes) monitored.

Control elements 415, 425, 435, as depicted in FIGS. 7-8 and discussed above, may be any suitable control element, such as electronically controllable valves, electronically controllable pump mechanisms, or the like.

Figure 9:
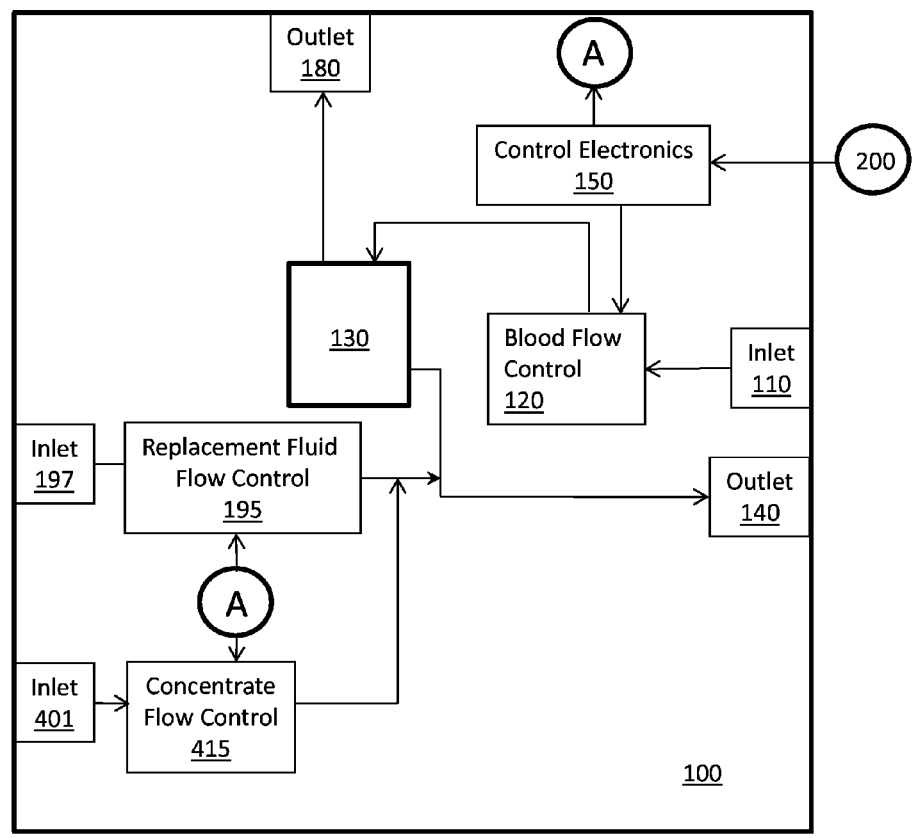
FIGS. 9-10 are schematic block diagrams of some components of blood fluid removal devices that are configured to adjust pH or electrolyte concentrations of fluids in response to data regarding monitored pH or electrolyte levels in blood.
Figure 10:
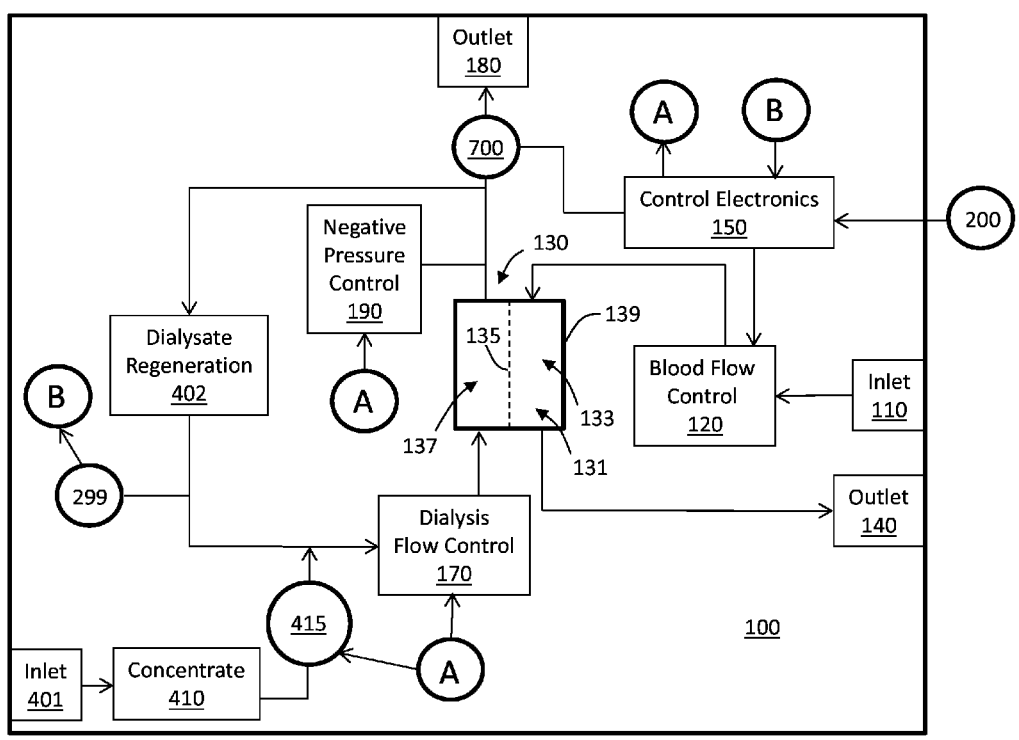

Any suitable system may be configured as depicted in FIGS. 7-8 to provide control of adjustment of pH or electrolytes based on data acquired from one or more sensors. By way of example, selected components of two example systems are illustrated in FIGS. 9-10. The system in FIG. 9 illustrates control of flow of a concentrate into replacement fluid, and the system in FIG. 10 illustrates control of flow of a concentrate into dialysate.

Referring now to FIG. 9, the depicted device 100 includes a fluid pathway for adding replacement fluid to blood before it is returned to the patient. The device 100 includes an inlet 110 for receiving blood from the patient and an outlet 140 for returning blood to the patient. In the flow path between the inlet 110 and outlet 140 are a blood flow control element 120 and a medium for removing fluid and contaminants from the blood. The blood flow control element 120 is operably coupled to control electronics 150 which provide instructions to control the rate at which blood is passed through medium 130. Fluids and contaminants removed from the blood by the medium 130 may exit via outlet 180.

The device 100 depicted in FIG. 9 also includes an inlet 197 for receiving bulk replacement fluid and a replacement fluid flow control element 195 in communication with the inlet and configured to control the rate at which the replacement fluid is added to the blood. The control electronics 150 are operably coupled to the replacement fluid flow control element 195 and are configured to control the rate at which replacement fluid flow control element 195 adds fluid to the blood. The device 100 also includes (i) an inlet 401 for receiving a concentrate for adjusting the pH or electrolyte concentration of the bulk replacement fluid, and (ii) a concentrate flow control element 415 in communication with the inlet 401 and configured to control the rate at which the concentrate is added to the replacement fluid or blood before the blood is returned to the patient. Preferably, the concentrate is added to the replacement fluid prior to the replacement fluid being added to the blood (as depicted) so that the concentrate may be mixed or diluted prior to being added to the blood. The device may include a mixer (not shown) to mix the concentrate and bulk replacement fluid prior to adding to the blood.

In the device depicted in FIG. 9, the control electronics 150 are operably coupled to the concentrate flow control element 415 and are configured to control the rate at which the concentrate flow control element 415 adds fluid to the replacement fluid or blood based on data received from one or more sensors 200 that monitor pH or electrolytes levels (e.g., as described above). By controlling the rate at which the concentrate is introduced into replacement fluid or blood, the concentration or pH (or buffering capacity) of the returned blood can be controlled.

Figure 12:
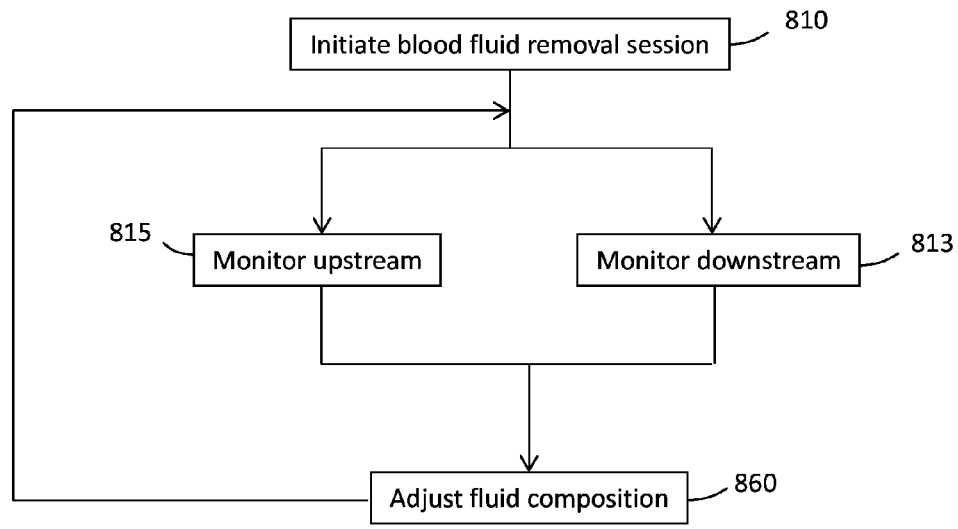

Referring now to FIG. 10, in which components that are numbered the same as in FIG. 12 refer to the same or similar components, a schematic block diagram of selected components of a blood fluid removal device 100 is shown. In the embodiment depicted in FIG. 13, the device has an inlet 110 for receiving blood from a patient, a blood flow control element 120 in communication with the inlet 110 and configured to control the rate at which blood flows through medium 130 for removing fluid and contaminates from the blood. The device also includes an outlet 140 in communication with the medium 130 for returning blood to the patient. In the depicted embodiment, the medium 130 component has a housing 139 defining a major chamber 131. A semipermeable filter 135, such as a hemodialysis or hemodiafiltration membrane filter, sealingly divides the major chamber into two minor chambers 133, 137; one 133 for blood flow and the other 137 for dialysate flow (as well as fluid and waste that passes through the filter 135 from the blood)

In the embodiment depicted in FIG. 10, used dialysate is regenerated by passing through dialysate regeneration medium 402 or components, such REDY regeneration medium and components, or the like, to regenerate bulk dialysate. The device also has an outlet 180 in communication with the medium 130 for diverting fluid removed from the blood out of the device. A flow regulator element 700, such as a valve, is operably coupled to control electronics 150 and is disposed in the flow path between the medium 130 and the outlet 180 to control the amount of fluid that exits the device (as a portion of the fluid is regenerated). Often, the regeneration media or components (402) remove much of the pH buffer or electrolytes from the dialysate. Accordingly, a concentrate containing concentrated electrolytes and pH buffers is added to the regenerated dialysate before the dialysate re-enters the medium 130. In some embodiments, a sensor 299 is positioned downstream of the regeneration medium 402 to monitor a level of a component of the regenerated dialysate. The sensor 299 may be a pH or electrolyte sensor and data acquired from sensor 299 may be used in determining how much concentrate to add to the regenerated fluid (which data may be provided to control electronics 150). The sensor 299 may be a sensor that monitors a blood waste product, such as urea, to determine whether the regeneration media 402 is properly functioning. Increased or detectable levels of a waste product may indicate that the regeneration media 402 or components may need replacement or regeneration.

In the depicted embodiment, the concentrate 410 is stored in a reservoir 410, having an inlet 401 that allows the concentrate supply in the reservoir 410 to be replenished from time to time. The rate at which the concentrate is added to the regenerated dialysate is controlled by concentrate flow control element 415, which is operably coupled to control electronics 150, and is based on data received from sensor 200 that monitors pH or electrolyte concentrations (e.g., as described above).

The device 100 in FIG. 10 also has a dialysis flow control element 170 for controlling the rate at which dialysis is introduced into the dialysis flow compartment of the medium 130.

In the depicted embodiment, the device 100 also includes a negative pressure control element 190 in communication with the dialysate compartment of the medium component 130. The negative pressure control element 190, which may include a pump or the like, may be used to generate or change a pressure differential across the membrane to control the rate at which fluid is removed from blood that passes though the medium component 130.

The control electronics 150, which may include a processor, memory, etc., are operably coupled to, and configured to control, the blood flow control element 120, the dialysis flow control element 170, and the negative pressure control element 190. By controlling these elements in a coordinated manner, the rate at which fluid is removed from blood may be controlled. It will be understood that a device 100 need not have all of the controllable elements (120, 170, 190) depicted in FIG. 10 to effectively control rate of fluid removal from blood.

Any suitable control element may be used for the various control elements (120, 150, 170, 195, 415) depicted in FIGS. 9-10. For example, a variable or adjustable rate pump may be employed. Alternatively or in addition, a series of electronically controllable valves may be employed. In some embodiments, the valves are in communication flow paths having differing flow resistances.

While FIGS. 9-10 show devices that can adjust blood electrolyte or pH by adjusting the pH or electrolyte concentration of replacement fluid or dialysate, it will be understood that pH and concentration can also be adjusted by, for example, adjusting the rate at which dialysate or blood is passed over a dialysis membrane. The rate of transfer between blood and dialysate of electrolytes, etc. across the membrane will be dependent on the flow rate of the blood and the dialysate. Accordingly, in systems where dialysate electrolyte concentration or pH cannot be readily adjusted, the rate of flow of blood or dialysate flow may be altered to achieve similar effects to adjusting the concentration of electrolytes in dialysate.

While FIGS. 9-10 depict components as being within a single unit, it will be understood that one or more of the components may be housed in separate units. For example, the control electronics, or a portion thereof, may be housed in a separate device, such as a computer, tablet, physician programmer, or the like. The computer, tablet, etc. may receive input from sensors, determine appropriate action to take, and instruct appropriate components of a blood fluid removal device to take the appropriate action.

It will be understood that the blood fluid removal devices and systems, and components thereof, described herein are presented for purposes of illustration and not limitation. Components, devices and systems other than those described herein, or derivations of the components, devices and systems described herein, may be employed. Further, components of the devices depicted and discussed above may be interchanged, substituted or added to components of alternative embodiments, as appropriate. Further, it will be understood that, while many of the blood fluid removal devices depicted in a variety of the figures, such as FIGS. 1-3 and 5-6, are shown as external to the patient, the teachings presented herein apply if the device, or components thereof, were implanted in the patient.

The devices and systems described above, or components thereof, may be used to carry out the methods depicted in FIGS. 11-13 and described below, or portions thereof. Of course, any suitable device or system may be employed to carry out the methods, or portions thereof, described below. It will be understood that various steps of the methods presented with regard to any one of FIGS. 11-13 below may be interchanged, substituted, or added to steps presented with regard to any other of FIGS. 11-13.

Figure 11:
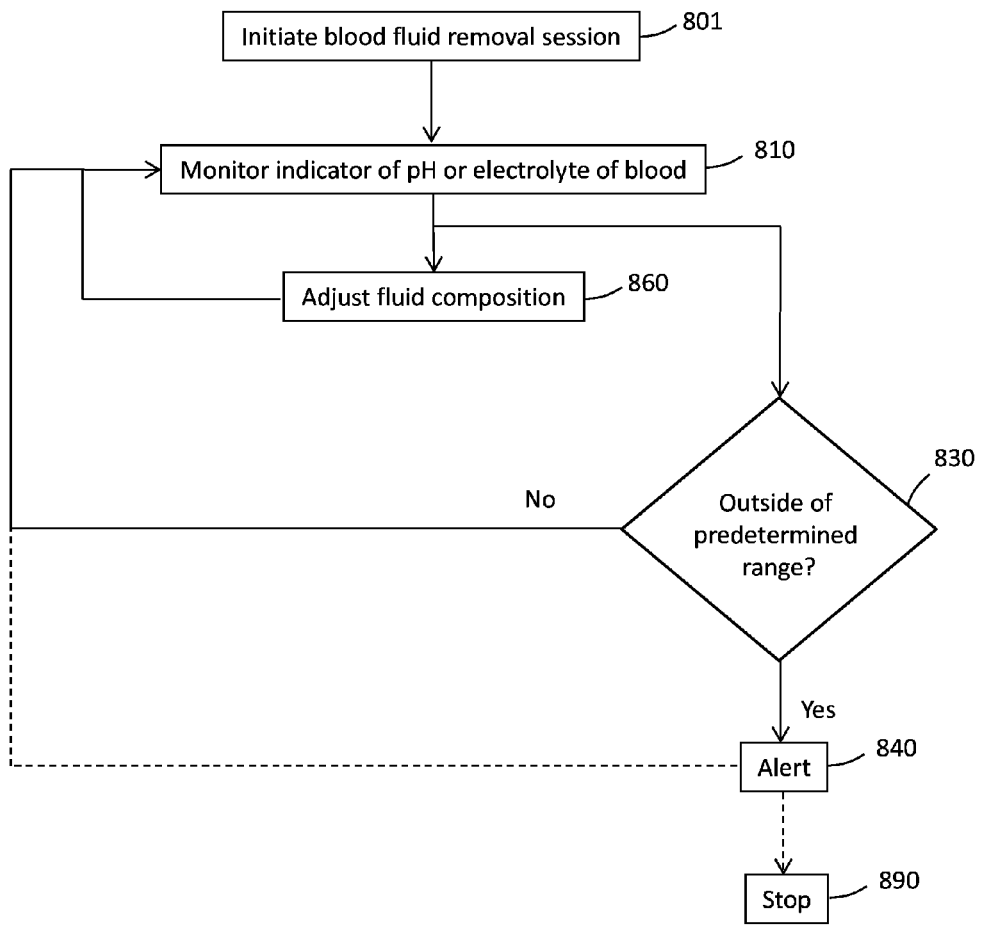
FIGS. 11-13 are flow diagrams illustrating overviews of general methods in accordance with embodiments described herein.

Referring now to FIG. 11, the depicted method includes initiating a blood fluid removal session (801) and monitoring an indicator pH or electrolyte concentration of blood (810); e.g. detecting pH or electrolytes in blood or in fluid from which pH or electrolyte levels in blood can be derived. Based on the monitored indicator of pH or electrolytes, the pH or electrolyte composition or concentration of fluid (e.g., dialysate or replacement fluid) used in the blood fluid removal session may be adjusted (860). For example, based on one or more of the current value of a monitored ionic species or the rate of change in the monitored ionic species, the fluid composition may be adjusted, e.g. as discussed above.

As shown in FIG. 11, continuous, periodic or intermittent determinations may be made as to whether the pH or electrolyte concentration is out of range (830) based on data acquired during the monitoring (810). For example, a determination (830) may be made as to whether pH or electrolyte levels crossed a threshold (e.g., a ceiling or floor). If the pH or electrolytes are determined to be within range, monitoring (810) may continue. If the pH or electrolytes are determined to be out of range (e.g., cross a threshold), an alert (840) may be issued to notify the patient or a healthcare provider of the situation. In some cases, the situation may warrant stopping (890) of the blood fluid removal session; e.g., if the detected pH or electrolytes are too far out of range or cross a heightened threshold. In other cases, it may be suitable to continue with the blood fluid removal session with heightened awareness of a situation for which increased attention may be warranted.

Referring now to FIG. 12, the depicted method includes initiating a blood fluid removal session (801) and monitoring an indicator pH or electrolyte concentration upstream (815) and downstream (813) of blood fluid removal. Data acquired from upstream and downstream sensors may be compared to determine how to adjust (860) the fluid composition, e.g. as described above.

Figure 13:
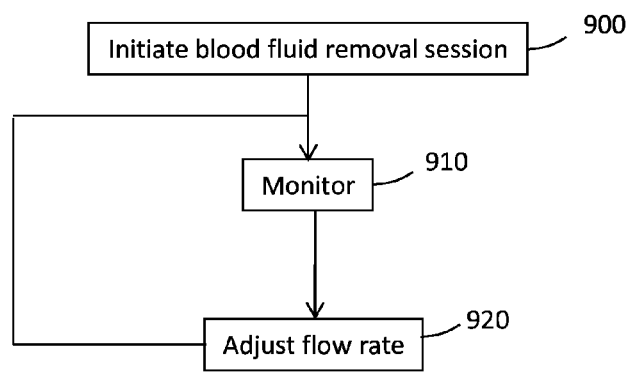

Referring now to FIG. 13, the depicted method show a method where blood electrolyte concentration or pH is adjusted by altering the flow rate of dialysate or blood. The method includes initiating a blood fluid removal session (900), such as a hemodialysis session, and monitoring an indicator of pH or electrolyte (910), which can be in the patient, upstream of the device, downstream of the device, within the device, or the like. Based on the monitored data (910), adjustments to the flow of dialysate or blood may be made (920) to adjust the electrolyte concentration or pH in the blood that gets returned to the patient.

The methods described herein, including the methods depicted in FIGS. 11-13, may be carried out by sensor devices, blood fluid removal devices, or other devices in communication with sensor devices or blood fluid removal devices. These methods may be algorithms or instructions programmed into memory of such devices, which may be carried out by processors or other control electronics of the devices. Preferably, the processor is in communication with appropriate control elements of the devices and is configured to control such elements in a manner such that the programmed instructions are carried out by the appropriate device. It will be understood that a computer readable medium programmed with instructions that cause a sensor device, blood fluid removal device, or other suitable device to carry out a method, or a portion thereof, as described herein are contemplated. The computer readable medium may be non-transitory, i.e. lasting for more than a fleeting instant or seconds. The medium may be memory, such as RAM or ROM, a cd or dvd, flash memory, or the like.

A variety of aspects of methods, systems, devices, computer-readable media and the like are disclosure herein. A summary of some of the aspects is provided below.

In a first aspect, a system comprises: (a) a blood fluid removal device comprising (i) an inlet for receiving blood from a patient, (ii) an outlet for returning blood from the patient, (iii) a medium for removing fluid and contaminants from the blood, the medium being positioned between the inlet and the first outlet, and (iv) a fluid source for carrying a fluid, the fluid selected from dialysate and replacement fluid, wherein if the fluid is dialysate the fluid source carries the fluid to the medium, and wherein if the fluid is replacement fluid the fluid source carries the fluid to the blood after the blood exits the medium; (b) a concentrate source for housing a concentrate solution comprising concentrated electrolyte or pH buffer; (c) a concentrate flow control element for controlling the rate that the concentrate solution enters the fluid source; (d) a first sensor configured to monitor an indicator of blood electrolyte concentration or blood pH; and (e) control electronics in operable communication with the sensor and the concentrate flow control element, wherein the control electronics are configured, via the concentrate flow control element, to adjust the rate at which the concentrate solution enters the fluid source based on data obtained from the sensor.

A second aspect is a system of the first aspect, wherein the first sensor is configured to monitor blood before the blood enters the medium.

A third aspect is a system of the second aspect, further comprising a second sensor configured to monitor an indicator of blood electrolyte concentration or blood pH, the second sensor being configured to monitor blood after the blood exits the medium.

A fourth aspect is a system of the third aspect, wherein the control electronics are in operable communication with the second sensor and are configured to compare data acquired from the first sensor to data acquired from the second sensor, and wherein the control electronics are configured to adjust the rate at which the concentrate solution enters the fluid source based on the comparison of the data acquired from the first sensor and the second sensor.

A fifth aspect is a system of aspect 1, wherein the first sensor is configured to monitor the indicator in fluid removed from the blood after the fluid removed from the blood exits the medium A sixth aspect is a system of aspect 5, wherein the control electronics are configured to derive the blood pH or blood electrolyte concentration based on data acquired from the first sensor.

A seventh aspect is a system of aspect 5, further comprising a second sensor configured to monitor the indicator in dialysate in the fluid source before the dialysate enters the medium, wherein the control electronics are control electronics are in operable communication with the second sensor and are configured to compare data acquired from the first sensor to data acquired from the second sensor, and wherein the control electronics are configured to adjust the rate at which the concentrate solution enters the fluid source based on the comparison of the data acquired from the first sensor and the second sensor.

An eighth aspect is a system of the first aspect, wherein the first sensor is configured to monitor the indicator in the blood after the blood exits the medium and before replacement fluid is added to the blood.

A ninth aspect is a system of aspect 8, further comprising a second sensor configured to monitor the indicator in the blood after the replacement fluid has been added to the blood.

A tenth aspect is a system of any of aspects 1-9, wherein the control electronics, or components thereof, are housed within a housing of the blood fluid removal device.

An eleventh aspect is a system of any of aspects 1-10, further comprising a computer readable medium, wherein the computer readable medium comprises instructions that cause the control electronics to control the concentrate flow control element to adjust the rate at which the concentrate solution enters the fluid source based on data obtained from the sensor.

A twelfth aspect is a method carried out by a blood fluid removal device or system, comprising: (i) initiating blood fluid removal procedure for a patient in need thereof, wherein the procedure comprise use of a fluid selected from a dialysate fluid or a replacement fluid, and wherein the fluid has an initial pH buffer composition or electrolyte composition; (ii) monitoring an indicator of blood electrolyte concentration or blood pH of the patient during the blood fluid removal session; and (iii) adjusting the pH buffer composition or the electrolyte composition of the fluid based on a value of the monitored indicator.

A thirteenth aspect is method of aspect 12, wherein monitoring the indicator comprises monitoring the indicator in blood before passing the blood through a blood fluid removal medium and after passing the blood through the blood fluid removal medium A fourteenth aspect is a method of aspect 13, further comprising comparing a value of the indicator monitored before the blood is passed through the medium to a value of the indicator monitored after passing the blood through the medium, wherein adjusting the pH buffer composition or the electrolyte composition comprises adjusting the composition based on the comparison.

A fifteenth aspect is a method of any of aspects 12-14, wherein adjusting the composition comprises adding a concentrated electrolyte solution or buffer solution to the fluid.

A sixteenth aspect is a method of any of aspects 12-15, further comprising (i) determining whether a value of the monitored indicator crosses a threshold; and (ii) providing an alert if the value of the monitored indicator is determined to cross the threshold.

A seventeenth aspect is a method of aspect 12, wherein monitoring the indicator comprises monitoring the indicator in fluid removed from the blood.

An eighteenth aspect is a method of aspect 17, further comprising determining a blood electrolyte concentration or pH from a value of the monitored indicator of the fluid removed from the blood.

A nineteenth aspect is a method of aspect 17 or aspect 18, wherein the fluid for use in the blood fluid removal procedure is dialysate, and wherein monitoring the indicator further comprises monitoring the indicator in the dialysate prior to the dialysate entering a blood fluid removal medium, and wherein the method further comprises comparing a value of the monitored indicator in fluid removed from the blood to a value of the monitored indicator in the dialysate prior to entering the blood fluid removal medium.

A twentieth aspect is a method of aspect 12, wherein the fluid for use in the blood fluid removal procedure is replacement fluid, and wherein monitoring the indicator comprises monitoring the indicator in blood downstream of a blood fluid removal medium and upstream of addition of the replacement fluid to the blood.

A twenty-first aspect is a method of aspect 20, wherein monitoring the indicator further comprises monitoring the indicator in the blood downstream of the addition of the replacement fluid, wherein the method further comprises comparing a value of the monitored indicator obtained upstream of the addition of replacement fluid to a value of the monitored indicator obtained downstream of the addition of replacement fluid.

A twenty-second aspect is a system comprising: (i) a medium housing defining a major chamber; (ii) a blood flow removal membrane disposed in the housing and sealingly dividing the major chamber into first and second minor chambers; (iii) a first inlet and a first outlet in fluid communication with the first minor chamber, wherein the system is configured such that blood enters the first minor chamber through the first inlet and exits the first minor chamber through the first outlet; (iv) a second inlet and a second outlet in fluid communication with the second minor chamber, wherein the system is configured such that dialysate enters the second minor chamber through the second inlet and exits the second minor chamber through the second outlet; (v) a dialysate regeneration medium in fluid communication with and disposed in a dialysate flow path between the second inlet and the second outlet; (vi) a concentrate source for housing a concentrate solution comprising concentrated electrolyte or pH buffer; (vii) a concentrate flow control element for controlling the rate that the concentrate solution enters the dialysate flow path downstream of the dialysate regeneration medium and upstream of the second inlet; (viii) a sensor configured to monitor an indicator of electrolyte concentration or pH of dialysate in the dialysate flow path downstream of the dialysate regeneration medium and upstream of the second inlet; and (ix) control electronics in operable communication with the sensor and the concentrate flow control element, wherein the control electronics are configured, via the concentrate flow control element, to adjust the rate at which the concentrate solution enters the dialysate flow path based on data obtained from the sensor.

A twenty-third aspect is a method carried out by a blood fluid removal device or system, comprising: (i) initiating blood fluid removal procedure for a patient in need thereof, wherein the procedure comprises use of a dialysate fluid and a dialysate membrane, as at least a part of a blood fluid removal medium, across which electrolytes may be exchanged between blood and the dialysate fluid; (ii) monitoring an indicator of blood electrolyte concentration or blood pH during the blood fluid removal session; and (iii) adjusting the flow rate of the dialysate fluid or blood based on a value of the monitored indicator.

A twenty-fourth aspect is a method of aspect 23, wherein monitoring the indicator comprises monitoring the indicator in blood before passing the blood through the blood fluid removal medium and after passing the blood through the blood fluid removal medium.

A twenty-fifth aspect is a method of aspect 23, further comprising comparing a value of the indicator monitored before the blood is passed through the medium to a value of the indicator monitored after passing the blood through the medium, wherein adjusting the flow rate of the dialysate fluid or the blood comprises adjusting the composition based on the comparison.

A twenty-sixth aspect is a method of any of aspects 23-25, wherein monitoring the indicator comprises monitoring the indicator in fluid removed from the blood.

A twenty-seventh aspect is a method of aspect 23, further comprising determining a blood electrolyte concentration or pH from a value of the monitored indicator of the fluid removed from the blood.

Thus, systems, devices and methods for ELECTROLYTE AND pH MONITORING FOR FLUID REMOVAL PROCESSES are described. Those skilled in the art will recognize that the preferred embodiments described herein may be altered or amended without departing from the true spirit and scope of the disclosure, as defined in the accompanying claims.

In the claims that follow, the designators "first", "second", "third" and the like are used for purposes of distinguishing between elements and not for purposes of enumerating the elements or for defining a sequence of the elements. For example, a "third" sensor does not necessarily imply that there are three sensors but rather that the "third" sensor is distinct from the "first" sensor. By way of further example, a "third" sensor does not necessarily come later in time than a "first" sensor.

What is claimed is:

1. A system comprising:
   a blood fluid removal device comprising:
   (i) an inlet for receiving blood from a patient,
   (ii) an outlet for returning blood from the patient,
   (iii) a medium for removing fluid and contaminants from the blood, the medium being positioned between the inlet and the outlet, and
   (iv) a fluid source for carrying dialysate to the medium;
   a concentrate source for housing a concentrate solution comprising concentrated electrolyte or pH buffer;
   a concentrate flow control element for controlling the rate that the concentrate solution enters the fluid source;
   a first sensor configured to monitor an indicator of blood electrolyte concentration or blood pH in the blood before the blood enters the medium,
   a second sensor configured to monitor an indicator of blood electrolyte concentration or blood pH in the blood after the blood exits the medium and before a replacement fluid is added to the blood; and
   control electronics in operable communication with the first sensor and the concentrate flow control element,
   wherein the control electronics are configured, via the concentrate flow control element, to adjust the rate at which the concentrate solution enters the fluid source based on the rate of change of blood pH or blood electrolyte concentration based on data obtained from the first sensor and the second sensor.

2. The system of claim 1, wherein the control electronics are in operable communication with the second sensor and are configured to compare data acquired from the first sensor to data acquired from the second sensor, and wherein the control electronics are configured to adjust the rate at which the concentrate solution enters the fluid source based on the comparison of the data acquired from the first sensor and the second sensor.

3. The system of claim 1, wherein a third sensor is configured to monitor the indicator in fluid removed from the blood after the fluid removed from the blood exits the medium.

4. The system of claim 3, wherein the control electronics are configured to derive the blood pH or blood electrolyte concentration based on data acquired from the third sensor.

5. The system of claim 3, further comprising a fourth sensor configured to monitor the indicator in dialysate in the fluid source before the dialysate enters the medium, wherein the control electronics are in operable communication with the fourth sensor and are configured to compare data acquired from the third sensor to data acquired from the fourth sensor, and wherein the control electronics are configured to adjust the rate at which the concentrate solution enters the fluid source based on the comparison of the data acquired from the third sensor and the fourth sensor.

6. The system of claim 1, further comprising a third sensor configured to monitor the indicator in the blood after the replacement fluid has been added to the blood.

7. The system of claim 1, wherein the control electronics, or components thereof, are housed within a housing of the blood fluid removal device.

8. The system of claim 1, further comprising a computer readable medium, wherein the computer readable medium comprises instructions that cause the control electronics to control the concentrate flow control element to adjust the rate at which the concentrate solution enters the fluid source based on data obtained from the first sensor and the second sensor.

* * * * *